United States Patent
Faccioli et al.

(10) Patent No.: US 10,123,877 B2
(45) Date of Patent: Nov. 13, 2018

(54) SPACER DEVICE FOR TREATING INFECTIONS OF THE SHOULDER ARTICULATION

(71) Applicant: TECRES S.p.A., Sommacampagna (Verona) (IT)

(72) Inventors: Giovanni Faccioli, Monzambano (IT); Renzo Soffiatti, Nogara (IT)

(73) Assignee: TECRES S.P.A., Sommacampagna (VR) (IT)

(*) Notice: Subject to any disclaimer, the term of this patent is extended or adjusted under 35 U.S.C. 154(b) by 0 days.

(21) Appl. No.: 15/520,198

(22) PCT Filed: Aug. 28, 2015

(86) PCT No.: PCT/IB2015/056540
§ 371 (c)(1),
(2) Date: Apr. 19, 2017

(87) PCT Pub. No.: WO2016/063146
PCT Pub. Date: Apr. 28, 2016

(65) Prior Publication Data
US 2017/0304064 A1    Oct. 26, 2017

(30) Foreign Application Priority Data
Oct. 21, 2014 (IT) .............. VR2014A0259

(51) Int. Cl.
*A61F 2/40* (2006.01)
*A61F 2/30* (2006.01)

(52) U.S. Cl.
CPC .. *A61F 2/4014* (2013.01); *A61F 2002/30604* (2013.01); *A61F 2002/30607* (2013.01); *A61F 2002/30677* (2013.01); *A61F 2002/4022* (2013.01); *A61F 2310/00353* (2013.01)

(58) Field of Classification Search
CPC ....................................................... A61F 2/40
See application file for complete search history.

(56) References Cited

U.S. PATENT DOCUMENTS

2006/0069445 A1* 3/2006 Ondrla .................... A61F 2/40
                                                            623/19.12
2009/0192621 A1    7/2009 Winslow et al.

FOREIGN PATENT DOCUMENTS

EP          1639965       3/2006
WO       2014096912       6/2014

* cited by examiner

*Primary Examiner* — David Isabella
*Assistant Examiner* — Christine Nelson
(74) *Attorney, Agent, or Firm* — Tutunjian & Bitetto, P.C.

(57) ABSTRACT

Spacer device for the two-phase treatment of infections of anatomic and reverse shoulder prostheses, including a humeral component equipped with a stem, a head component and means for connecting or articulating the humeral component with the head component.

16 Claims, 4 Drawing Sheets

SPACER DEVICE FOR TREATING INFECTIONS OF THE SHOULDER ARTICULATION

TECHNICAL FIELD OF THE INVENTION

The present invention regards a spacer device for treating infections of the shoulder articulation, both deriving from anatomic prostheses or reverse prostheses, in particular for the so-called "two-stage" treatment.

STATE OF THE PRIOR ART

The currently-used hip prostheses are substantially of two types.

The first type is termed "conventional" and reproposes the normal anatomy of the shoulder. In particular, such prosthesis type provides for a humeral component constituted by a stem, to be inserted in the upper part or proximal epiphysis of the humerus, which is equipped with a hemi-spherical or half-spherical head, which reproduces the head of the humerus and acts as articulation of the stem of the prosthesis, and hence of the humerus, with the scapula, or better yet the glenoid cavity of the scapula, reforming the scapulohumeral articulation.

If the glenoid cavity is also damaged, this can be substituted by a glenoid cup or by a glenoid component, which reforms the integrity of the glenoid seat in which the head of the humeral component is articulated.

The second type of shoulder prosthesis is termed "reverse" and is used when the patient, in addition to arthrosis, simultaneously suffers lesions of greater size, such as large lesions of the rotator cuff.

For this type of patients, the "conventional" (or anatomic) shoulder prosthesis can cause pain and limited movement, while the prosthesis of "reverse" type allows overcoming such drawbacks.

Such second type of prosthesis provides that the glenoid component is equipped with a hemi-sphere or half-sphere, suitable for being articulated with a seat or cup obtained in the proximal end of the humeral component. Therefore, the humeral component is equipped with a cup or seat in which the head fixed to the scapula of the patient is articulated.

The "reverse" prosthesis relies on the deltoid muscle, and not on the rotator cuff that is damaged, in order to allow the movements between the shoulder and the arm.

Such "reverse" prosthesis type also allows greater preservation of the humerus bone, which is less damaged by the operation procedure (e.g. unlike the "conventional" prosthesis, whose planting requires the resecting of the head of the humerus). In such a manner, the preserved bone portion can be useful if it is subsequently necessary to proceed with the implant of a further "conventional" prosthesis.

The application n. US2009192621 discloses an implant assembly, for selectively performing reverse and traditional arthroplasty for a shoulder joint. The implant assembly includes several single pieces including a head, a cup, a humeral stem and an adaptor.

The European application n. EP1639965 discloses a shoulder arthroplasty kit for shoulder arthroplasty that includes a stem for insertion into the humerus and a first member with a surface having a convex periphery adapted for articulation with the natural glenoid fossa. The first member is removably cooperable with the stem. The kit also includes a second member including a portion having a concave periphery. The second member is removably cooperable with the stem. The kit further includes a third member for insertion into the natural glenoid fossa, having a portion with a convex periphery. The third member is adapted for articulation with the second member.

The International application n. WO2014096912 discloses a shoulder prosthesis, provided with a humeral stem having a conical proximal female seat suitable for interchangeably housing adaptors for the standard application of the shoulder prosthesis and reverse application of the shoulder prosthesis, respectively.

Both prosthesis types, however, can be subjected to infection and must therefore be explanted, and the infection site must be treated, in order to reach the implant of a new permanent prosthesis.

Such method for treating the infection is usually defined two-stage treatment, since it provides for a first stage of removing the infected prosthesis and a second stage of implanting a new prosthesis, once the infection has been eliminated. There is therefore the need to be able to use a temporary spacer device capable of replacing both a permanent prosthesis of "conventional" type and one of "reverse" type.

For such purpose, the spacer device performs the functions of maintaining the articular spaces as well as treating the bone infection by liberating quantities of antibiotic in the infected zone. With regard to the second function just indicated, the spacer is able to treat the infection underway by releasing antibiotic in an aimed manner and in infinitesimal quantities, while the application of doses of antibiotic that are even higher, but with methods that do not provide for the use of spacers, such as washing the infected site with high-dosage antibiotic solutions, does not allow obtaining the same results.

Studies conducted in the field have in fact detected that the bone tissue absorbs, in a concentrated manner, all the (even few) antibiotic molecules liberated daily by the spacer. Naturally, this is verified if the antibiotic is released by the spacer in contact or adjacent to the bone tissue, in which case the quantity of antibiotic locally attains the effective concentration for eradicating the infection. For this reason, it is essential that the spacer be extended over the entire area of the infection, this indicating that if the infected prosthesis is a long prosthesis, a long spacer will be used and if the infected prosthesis is of short type a short spacer will be used. If a short spacer was placed where a long prosthesis had previously been implanted, part of the bone would not be treated with antibiotic, thus leaving the bacteria free to proliferate.

For this reason, in particular in the case of the shoulder, if a reverse shoulder prosthesis has been infected, a shoulder spacer of anatomic or conventional type must not be used, since the antibiotic could never reach the glenoid zone.

SUMMARY OF THE INVENTION

One object of the present invention is to improve the state of the art.

Another object of the present invention is to provide a spacer device capable of replacing various shoulder prosthesis types, in particular, both the prosthesis of "conventional" or "anatomic" type and that of "reverse" type.

Still another object of the present invention is to design an effective, safe and inexpensive spacer device.

A further object of the present invention is to obtain a spacer device that allows maintaining the articular functionality by reducing the recovery times for the patient.

In accordance with one aspect of the invention, a spacer device is provided according to the present specification.

BRIEF DESCRIPTION OF THE DRAWINGS

Further characteristics and advantages of the invention will be clearer from the description of several embodiments of the present invention, illustrated by way of example in the enclosed drawings, in which.

DETAILED DESCRIPTION OF THE INVENTION

Figure 1:
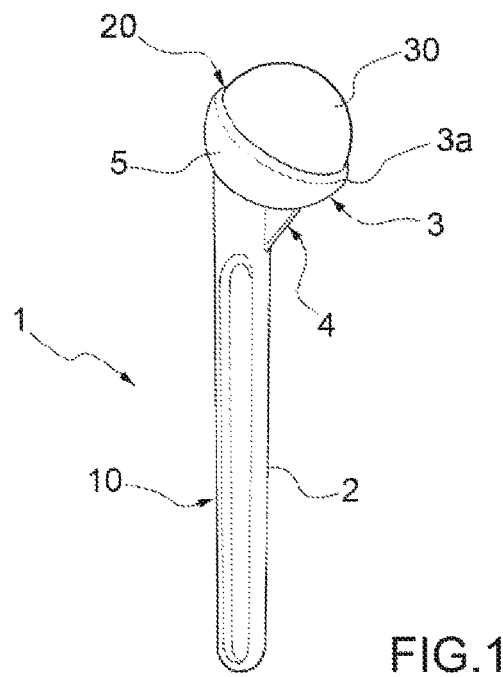
FIG. 1 is a perspective side view of a shoulder spacer device according to the present invention in a first operative configuration or anatomic configuration.
Figure 2:
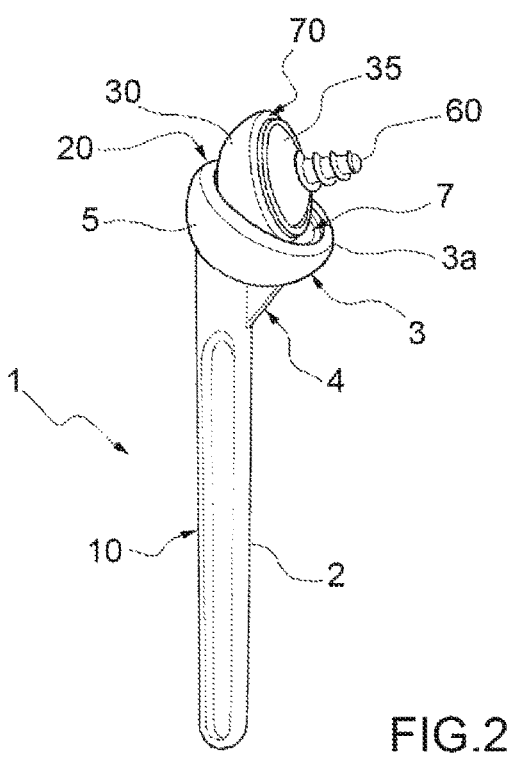
FIG. 2 is a perspective side view of a shoulder spacer device according to the present invention in a second operative configuration or reverse configuration.
Figure 3:
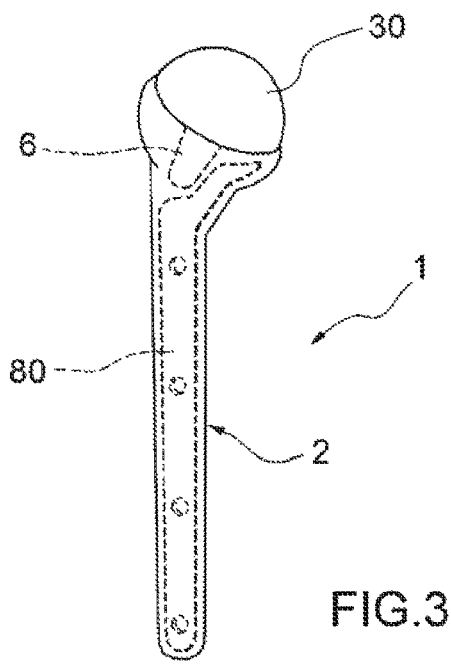
FIG. 3 is a partially transparent side view of the shoulder spacer device pursuant to FIGS. 1 and 2, in the first operative configuration.

With reference to the figures, reference number 1 indicates overall a shoulder spacer device according to the present invention, in particular a temporary spacer device to be used during the two-stage treatment of infections of anatomic and reverse shoulder prostheses, during the time from the explant of a first prosthesis and the implant of a second prosthesis, in order to treat the infection underway at the implant site.

The spacer device 1 is capable of maintaining the articular space and ensuring the articulation of the shoulder up to the implant of the new prosthesis, and at the same time capable of treating the infection due to the presence, in the spacer device itself, of suitable drugs or medications, such as one or more antibiotics. The device 1 according to the present invention is made of biologically compatible material, suitable of being added and/or additionable with one or more pharmaceutical products, active and/or therapeutic ingredients suitable for being released into the tissues of the patient adjacent to the device.

The biologically compatible material of the spacer device according to the invention is porous, in particular comprises pores that may or may not be interconnected.

The materials for the spacer device according to the present invention can be selected from among: metals, metallic alloys, organic metals, ceramic, glass, plastic materials.

In particular, the plastic materials can comprise at least one from among: thermoplastic polymers, such as acrylic resins, including all copolymers and acrylic mixtures, polyethylene, polypropylene, etc.

In one version of the invention, the biologically compatible material with which the spacer device 1 is obtained comprises a bone cement or polymethyl methacrylate.

The material of the spacer device according to the present invention can comprise one or more pharmaceutical products, active and/or therapeutic ingredients.

The pharmaceutical products, active and/or therapeutic ingredients can comprise antibiotics, antiseptics, bacteriostatic agents, bactericides, antimycotics, chemotherapeutic agents, e.g. gentamicin, vancomycin, etcetera, or other active ingredients.

The material of the spacer device, being porous, can be added with one or more of the pharmaceutical products, active and/or therapeutic ingredients during production stage, or afterward by the doctor at the time of use on the patient, e.g. via impregnation. If, moreover, the spacer device is already provided by the producer comprising a pharmaceutical product, an active and/or therapeutic ingredient, it can be subsequently added with further one or more pharmaceutical products, active and/or therapeutic ingredients.

Such further one or more pharmaceutical products, active and/or therapeutic ingredients have the object of enlarging the action spectrum or introducing a medication highly specific for the identified pathogenic agent. Examples of antibiotic additions can be: to the gentamicin originally present, the doctor adds vancomycin to oppose the Gram-positive bacteria, or clindamycin for opposing anaerobic bacteria. In order to add such further one or more pharmaceutical products, active and/or therapeutic ingredients, it is sufficient to immerse the spacer according to the present invention in an aqueous antibiotic solution. The solution will be absorbed together with the antibiotic in the mass of the spacer in a few minutes. The quantity of absorbed solution can be modified as desired by virtue of the structure of the material of the spacer itself. Optimal values are comprised between 1 and 60% by weight of solution absorbed over the weight of the spacer. In other words, if the spacer weighs 100 grams, in accordance with its structure, it can absorb from 1 to 60 grams of medicated aqueous solution. Possibly, such further substances can be different from the pharmaceutical products, active and/or therapeutic ingredients already comprised in the spacer device, in order to enlarge the range of activities thereof.

The spacer device 1 comprises a humeral component 10, a head component 30 and means for connecting or articulating 20 the humeral component 10 with the head component 30. In addition, such connection or articulation means 20 are placed between the humeral component 10 and the head component 30.

In particular, the spacer device 1 is formed by the aforesaid two components, i.e. by the humeral component 10 and by the head component 30, which are distinct components that are separate from each other.

In a version of the invention, the spacer device 1 comprises only the humeral component 10 and the head component 30; the connection or articulation means 20 are made in a single piece or enbloc respectively in the humeral component 10 and in the head component 30.

The connection or articulation means 20 connect the humeral component 10 to the head component 30 or articulate the humeral component 10 to the head component 30.

The humeral component 10 is equipped with a stem 2 and with a proximal portion 3, at its proximal end.

During use, the stem 2 is suitable for being at least partially inserted in the humeral bone while the proximal portion 3 is suitable for being directed towards the glenoid cavity of the patient.

Figure 4A:
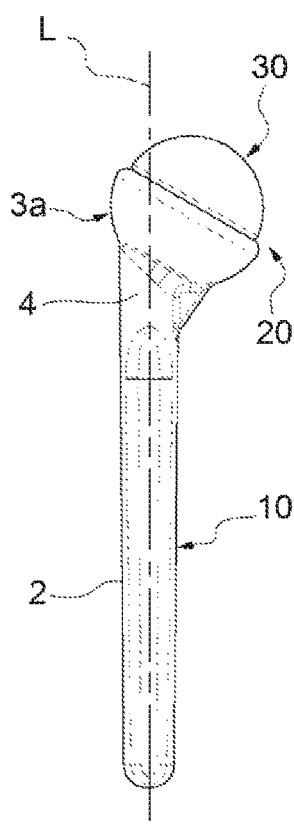
FIGS. 4A, 4B, 4C are side views of the shoulder spacer device in the first operative configuration (FIG. 4A) and in the second operative configuration (FIGS. 4B and 4C)
Figures 4B, 4C:
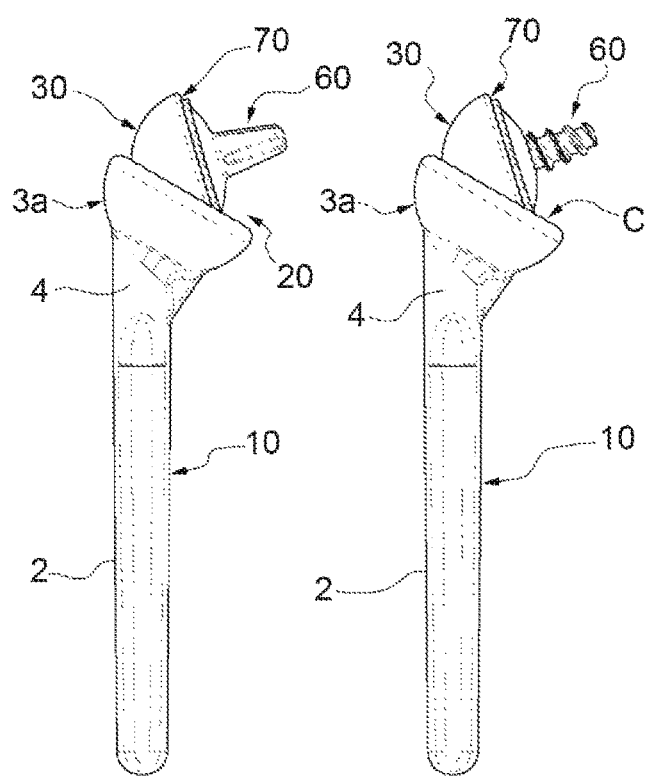

The stem 2 has, in one version of the invention, a cross section, taken according to a transverse plane perpendicular to the longitudinal axis L of the stem 2 (illustrated for example in FIG. 4A), that is substantially rectangular or polygonal.

The humeral component 10 comprises a joining portion 4. The joining portion 4 is positioned between the stem 2 and the proximal portion 3.

The joining portion 4 has, in one version of the invention, a cross section of greater size than the cross section of the stem 2. In such case, the joining portion 4 has "enlarged" size with respect to that of the stem 2.

The joining portion 4 determines a stiffening of the transition area between the stem 2 and the proximal portion 3 and an improved stability for the latter.

In one version of the invention, the humeral component 10 is obtained in a single piece, with the stem 2, the proximal portion 3 and the joining portion 4 stably constrained to each other.

In an alternative version, the humeral component 10 can be obtained in at least two pieces.

The proximal portion 3 has a configuration that is substantially cup-shaped 3a and/or comprises a perimeter side wall 5 which, during use, extends upward in the direction of the glenoid cavity starting from the stem 2 or better yet from the joining portion 4.

The wall 5 delimits a concave seat C.

The wall 5 has a configuration corresponding to part of the surface of a sphere, in particular it has a hemi-spherical or half-spherical or irregular configuration, whose concave seat C is facing or open towards the glenoid cavity.

In particular, the proximal portion 3, with cup shape 3a or hemisphere shape or half-sphere shape, regular, irregular or even incomplete, has a concavity or concave seat C that is hemi-spherical or half-spherical, regular, irregular or even incomplete. The concave seat C, during use, is suitable for at least partially containing or articulating with the head component 30; the concave seat C has radius ra.

The humeral component 10 or better yet the proximal portion 3 also comprises a recess or notch 6.

The recess or notch 6 extends from the concave seat C, in particular from its bottom wall, within the joining portion 4 towards the stem 2.

The connection or articulation means 20 comprise, in one version or first operative configuration, the recess or notch 6 and a protuberance 60 that extends from the head component 30.

The recess or notch 6 has a substantially cylindrical or frustoconical or nut screw configuration suitable for making a connection, stable in one version of the invention, with the head component 30, as better described hereinbelow.

Therefore, the joining portion 4 has a size or configuration "enlarged" with respect to the cross section of the stem 2 since it comprises, at its interior, the space that defines the aforesaid recess or notch 6. Therefore, the size of the joining portion 4 is greater than that of the stem 2 also in order to comprise the bulk of the recess or notch 6.

Figure 5:
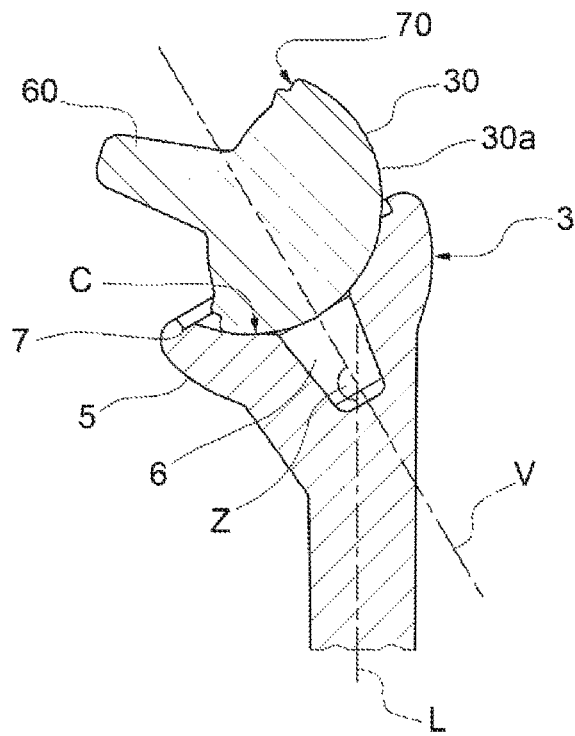
FIG. 5 is a sectional side view of a portion of the spacer device in the second operative configuration.
Figure 6:
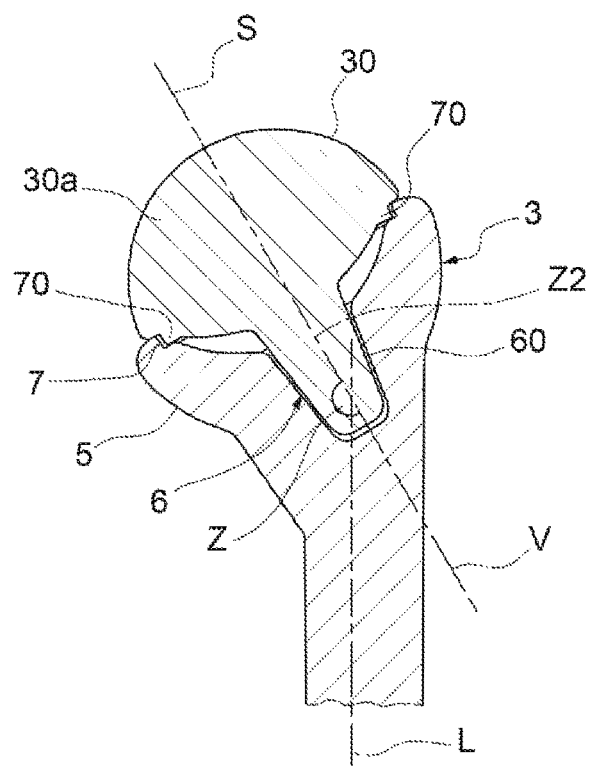
FIG. 6 is a sectional side view of a portion of the spacer device in the first operative configuration.

The recess or notch 6 extends inside the joining portion 4 towards the stem 2 according to an axis V (illustrated for example in FIGS. 5 and 6). The longitudinal axis L of the stem 2 and the axis V of the recess or notch 6 form an angle Z.

In one version of the invention, for example illustrated in FIG. 6, the axis V of the recess or notch 6 corresponds with the symmetry axis S of the head component 30 and with the symmetry axis Z2 of the protuberance 60.

Along the external perimeter or free peripheral edge of the wall 5 of the proximal portion 3, an annular step 7 is present. Such annular step is inside the wall 5 and hence within the concave seat C.

The shoulder spacer device 1 further comprises a head component 30 with hemi-spherical or half-spherical configuration.

The head component 30 comprises a convex surface 30a and a base 35.

In one version of the invention, the connection or articulation means 20 comprise the convex surface 30a and the concave seat C of the proximal portion of the humeral component 10, in a manner such that the surface 30a can be articulated and connected in a slidable or rotating manner with the concave seat C.

In the area or surface between the base 35 and the convex surface 30a, an annular shoulder 70 is present corresponding to and matching the annular step 7 present in the proximal portion 3.

The convex surface 30a is substantially matching the concave seat C of the proximal portion 3 of the spacer device 1.

In particular, the convex surface 30a is at least partially contained in the concave seat C, i.e. in the space or seat delimited by the wall 5 of the proximal portion 3. Therefore, the radius ra of the concave seat C is slightly greater than the radius rb of the head component 30 or better yet of its convex surface 30a.

A protuberance 60 extends perpendicularly from the base 35 towards the outside. The protuberance 60 has a substantially circular or frustoconical or screw configuration corresponding to and matching the recess or notch 6 of the proximal portion 3, or suitable for making a connection with the humeral component 3 or with the glenoid cavity of the patient.

In particular, the protuberance 60 is suitable for being inserted, according to a first operative configuration, for example illustrated in FIGS. 1, 3, 4A and 6 of the drawings enclosed herein, in the recess or notch 6 of the proximal portion 3, thus making the connection between the proximal portion 3 and the stem 2 of the humeral component 10.

In such first operative configuration, the spacer device 1 according to the present invention can be implanted and replace a shoulder prosthesis of "conventional" or "anatomic" type, when this must be explanted due to an infection. In such case, the humeral component 10, by means of the convex surface 30a of the head component 30 would be articulated with the glenoid cavity of the scapula of the patient.

Figure 7:
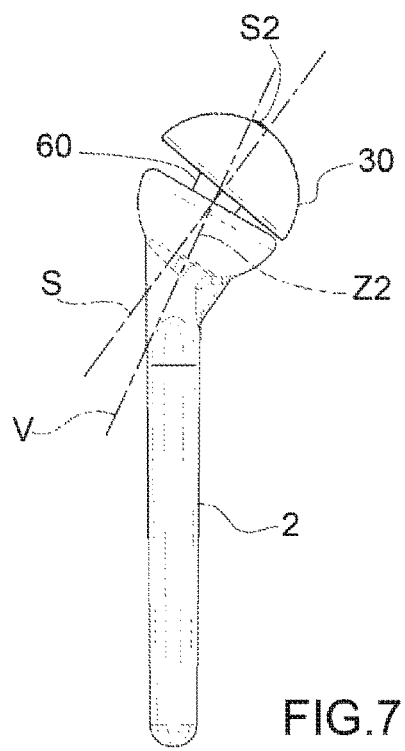
FIG. 7 is a side view of one version of the shoulder spacer device in the first operative configuration according to the present invention.
Figure 8:
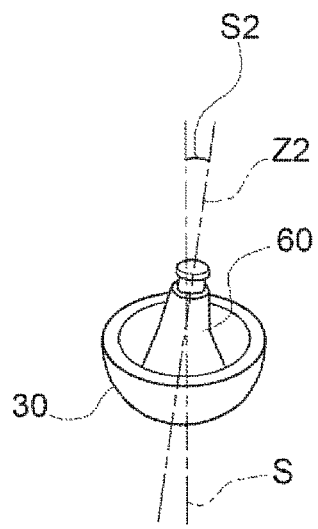
FIG. 8 is a perspective view of one component of the spacer device of FIG. 7.

In a further version of the invention, for example illustrated in FIGS. 7 and 8, the axis V of the recess or notch 6 corresponds with the main symmetry axis Z2 of the protuberance 60 but does not correspond with the symmetry axis S of the head component 30. In such case, the protuberance 60 is tilted, with respect to the symmetry axis S of the head component 30, by an angle S2. Such configuration allows angling the head component 30 with respect to the humeral component 10 in a manner so as to more correctly support the anatomy of the patient and the surgical requirements of the implant.

Figure 9:
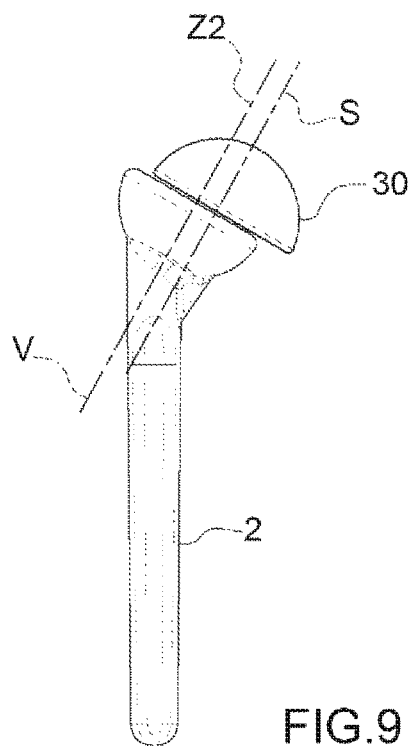
FIG. 9 is a side view of a further version of the shoulder spacer device in the first operative configuration according to the present invention.
Figure 10:
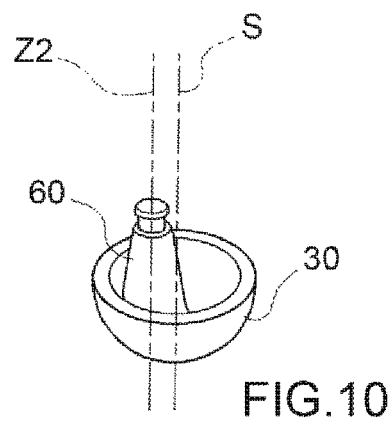
FIG. 10 is a perspective view of a component of the spacer device of FIG. 9.

In a still further version of the invention, for example illustrated in FIGS. 9 and 10, the axis V of the recess or notch 6 corresponds with the symmetry axis Z2 of the protuberance 60 but these do not correspond with the symmetry axis S of the head component 30: the symmetry axis S of the head component 30, in fact, is parallel but offset with respect to the symmetry axis Z2 of the protuberance 60. In such a manner, the protuberance 60 is eccentric with respect to the center of the base 35 or of the head component 30; the head component 30 is offset with respect to the concave seat C of the proximal portion 3 of the humeral component 2 and therefore it projects laterally with respect thereto. Also this version allows more correctly supporting the anatomy of the patient and the surgical requirements of the implant.

In such versions, the protuberance 60 preferably does not have a thread, such that the protuberance 60 can be inserted according to any orientation and position in the recess or notch 6 without having to rotate and hence without coming into contact or rubbing with the edges of the wall 5, which could occur if it was necessary to screw the protuberance 60.

The spacer device 1 according to the present invention, however, can also be used in a second operative configuration, illustrated in FIGS. 2, 4B, 4C and 5 of the enclosed drawings, when the head component 30 is inserted in the cup-shaped 3a or hemi-spherical or half-spherical configuration of the proximal portion 3, such that the convex surface 30a of the head component 30 is placed in contact and suitable for being slidably articulated with the concave seat C of the proximal portion 3.

In this version, the protuberance 60 of the head component 30 externally projects and is suitable for being inserted in the glenoid cavity of a patient's shoulder. Therefore, in the first operative configuration of the spacer device 1, the protuberance 60 is inserted in the recess or notch 6 and the convex surface 30a of the head component 30 recreates the head of the stem 2 (and hence of the humerus of the patient) in a substantially continuous manner, coming to realize an articulation surface with the glenoid cavity of the patient itself.

In the second operative configuration, instead, the spacer device 1 according to the present invention can be implanted and replace a shoulder prosthesis of "reverse" type, when this must be explanted due to an infection.

In such case, the protuberance 60 is inserted in the glenoid cavity and therefore the convex surface 30a is articulated within the concave seat C of the proximal portion, which is fixed, by means of the stem 2, to the patient's humerus.

As is visible in FIG. 6, if it is desired to use the spacer device 1 according to the present invention according to its first operative configuration, analogous to that of a "conventional" shoulder prosthesis, the protuberance 60 of the head component 30 is inserted in the recess or notch 6. Subsequently, the annular step 7 of the proximal portion 3 is brought into contact with or abutment against the annular shoulder 70 of the head component 30, possibly all this is fixed by means of bone cement or an adhesive component suitable for such purpose.

In such a manner, the convex surface 30a is arranged for being articulated and coming into contact with the glenoid cavity of the patient's scapula.

As is visible in FIG. 5, however, if it is desired to use the spacer device 1 according to the present invention according to its second operative configuration, analogous to that of a "reverse" shoulder prosthesis, the convex surface 30a of the head component 30 is placed in contact with or abutted against the internal surface of the concave seat C of the proximal portion 3, i.e. the head component 30 is inserted, with its convex surface 30a facing towards the stem 2, in the cup-shaped 3a or hemi-spherical or half-spherical configuration of the proximal portion 3. The convex surface 30a is then rotated and oriented in the concave seat C until the protuberance 60 has the desired tilt such that it can be inserted in the glenoid cavity of the patient and then the convex surface 30a of the head component 30, which is constrained to the glenoid cavity e.g. by means of bone cement or other suitable adhesive means, is arranged for being articulated and coming into contact with the concave seat C of the proximal portion 3 of the spacer device 1, such proximal portion 3 being in turn constrained, by means of the stem 2, to the humerus of the patient.

The protuberance 60 can be configured as a Morse taper (e.g. illustrated in FIG. 4B), suitable for being fit in the recess or notch 6 of the proximal portion 3.

In an alternative version of the invention, the protuberance 60 can have a thread (e.g. illustrated in FIG. 4C) suitable for being screwed to a corresponding nut screw provided in the internal surface of the recess or notch 6 (nut screw not illustrated).

In a still further version of the invention, the protuberance 60 can have a thread or a Morse taper configuration in order to be screwed or fittingly locked in the glenoid cavity of the patient, according to the second operative configuration of the spacer device 1 according to the present invention.

In order to improve the stability of the implant, the load resistance and to therefore ensure a good quality of life to the patient even between the time of the explant of a first shoulder prosthesis and the insertion of a second shoulder prosthesis, the spacer device 1, in particular the stem 2 and/or the joining portion 4, have a reinforcing core 80 inserted within the stem 2 and/or the joining portion 4.

In particular, such reinforcing core 80 can be metallic, when the biologically compatible material that composes the spacer device 1 is a plastic material or when it is deemed necessary.

The head component 30 and/or the concave seat C can be equipped with a polymer coating, e.g. ultra high molecular weight polyethylene (UHMW-PE) in order to render the articulation surface between the convex surface 30a and the internal surface of the concave seat C, or between the convex surface 30a and the glenoid cavity, smoother and more slidable.

It is thus seen that the spacer device 1 according to the present invention attains the provided objects. In particular, the doctor is able to use a single spacer device, both in situations of explant of a shoulder prosthesis of "conventional" type, and of that of "reverse" type. Hence, with regard to maintaining both possibilities open, the magazine spaces for storing such spacer devices and also the costs are considerably reduced, since it is sufficient to have a single spacer model for both operation types. In addition, in the case of replacement of the reverse prosthesis, it is possible to adjust the insertion angle of the head component 30 on the glenoid cavity of the patient, in a manner so as to render such insertion more adhering to the anatomy or to the operational needs of the patient itself.

Indeed, as stated above, the spacer must be extended for the entire area of the infection underway, and with the traditional spacers, different spacers must be used in order to treat an infection in the area occupied by a prosthesis of conventional type or of reverse shoulder type; according to the present invention, however, due to the presence of the aforesaid connection or articulation means, one spacer allows treating both infections (at the site of a conventional prosthesis or at that of a reverse shoulder prosthesis) with the same spacer.

The present invention thus conceived is susceptible of numerous modifications and variations, all falling within the protective scope of the claims.

In particular, characteristics described for one version of the invention can also be combined with other versions, without departing from the protective scope of the following claims.

The invention claimed is:

1. A spacer device for the two-stage treatment of infections of shoulder prostheses, comprising a humeral component equipped with a stem,
a proximal portion and a joining portion, said stem being suitable for insertion into a humerus of a patient, wherein said proximal portion, includes a cup-shape surface forming concave seat wherein said joining portion is positioned between said stem and said proximal portion, wherein said spacer device further comprises a head component having opposite connection and articulation means and said connection means comprising a protuberance configured to be disposed in a recess or notch formed in said concave seat within the joining portion towards said stem or configured to connect a glenoid cavity of a patient, and wherein said articulation means comprising a convex articulating surface configured to engage either the glenoid cavity or said concave seat of said proximal portion, wherein, said proximal portion and said joining portion are stably constrained to each other, wherein said concave seat, during use, is suitable for at least partially containing said head component or articulating with said convex articulating surface of said head component.

2. The spacer device according to claim 1, wherein said connection or articulation means are arranged between said humeral component and said head component.

3. The spacer device according to claim 1, wherein said head component has a hemi-spherical or semi-spherical configuration and/or wherein said head component comprises a convex surface, and axis of symmetry (S) and a base and/or wherein said convex surface has a hemi-spherical or semi-spherical configuration substantially matching the configuration of said concave seat (C).

4. The spacer device according to claim 3, wherein said head component comprises said protuberance that extends perpendicularly from said base.

5. The spacer device according to claim 3, wherein said convex surface is inserted in said concave seat (C) and articulates with it.

6. The spacer device according to claim 3, wherein between said base and said convex surface there is an annular shoulder corresponding to and matching said annular step of said proximal portion.

7. The spacer device according to claim 3, wherein in said second operative configuration said head component is inserted in said cup-shaped or hemi-spherical or semi-spherical configuration, so that the convex surface of said head component is placed in contact and suitable for being slidably articulated with said concave seat (C) of said proximal portion.

8. The spacer device according to claim 1, wherein said connection or articulation means comprise a convex surface and said concave seat (C) of said proximal portion of said humeral component.

9. The spacer device according to claim 1, wherein said recess or notch extends inside one of said joining portion or inside said proximal portion of said humeral component.

10. The spacer device according to claim 1, wherein said protuberance has a substantially cylindrical or frustoconical or screw configuration or a configuration suitable for making a connection with said humeral component or with the glenoid cavity of the patient.

11. The spacer device according to claim 1, wherein said proximal portion comprises an annular step arranged at the free peripheral edge or outer perimeter of said wall.

12. The spacer device according to claim 1, comprising a reinforcing inner core.

13. The spacer device according to claim 1, comprising a biologically compatible material, suitable of being added and/or additionable with one or more pharmaceutical products, active and/or therapeutic ingredients at the production stage of the device and/or afterwards, at the time of use, suitable for being released into the tissues of the patient, and/or wherein said biologically compatible material is porous or comprises pores that may or may not be interconnected, and/or wherein said biologically compatible material is selected among: metals, metallic alloys, organic metals, ceramic, glass, plastic materials, thermoplastic polymers, acrylic resins, copolymers and acrylic mixtures, polyethylene, polypropylene, bone cement, polymethyl methacrylate.

14. The spacer device according to claim 1, wherein said humeral component and said head component can be arranged in a first operative configuration to replace a conventional shoulder prosthesis, as well as in a second operative configuration to replace a reverse shoulder prosthesis.

15. The spacer device according to claim 1, wherein in said first operative configuration said protuberance is inserted in said recess or notch, thus making the connection between said head component and said humeral component.

16. The spacer device according to claim 1, wherein said recess or notch has at least one of a substantially cylindrical or frustoconical or nut screw configuration.

* * * * *